United States Patent [19]

Fishman

[11] Patent Number: 5,344,236
[45] Date of Patent: Sep. 6, 1994

[54] METHOD FOR EVALUATION OF QUALITY OF THE INTERFACE BETWEEN LAYER AND SUBSTRATE

[76] Inventor: Iiya M. Fishman, 558 Cambridge Ave., Palo Alto, Calif. 94306

[21] Appl. No.: 824,373

[22] Filed: Jan. 23, 1992

[51] Int. Cl.$^5$ .................. G01N 25/20; G01N 25/72
[52] U.S. Cl. ........................................ 374/5; 374/7; 374/4; 356/237; 356/432
[58] Field of Search .................. 374/6, 7, 4, 5; 356/237, 432

[56] References Cited

U.S. PATENT DOCUMENTS

| | | | |
|---|---|---|---|
| 3,795,133 | 3/1974 | Fergason et al. | 374/7 |
| 3,978,713 | 9/1976 | Penney | 374/7 |
| 4,468,136 | 8/1984 | Murphy et al. | 374/6 |
| 4,484,820 | 11/1984 | Rosencwaig | 374/6 |
| 4,513,384 | 4/1985 | Rosencwaig | 364/563 |
| 4,521,118 | 6/1985 | Rosencwaig | 374/5 |
| 4,522,510 | 6/1985 | Rosencwaig et al. | 374/7 |
| 4,538,912 | 9/1985 | Shaw, Jr. | 356/237 |
| 4,579,463 | 4/1986 | Rosencwaig et al. | 374/5 |
| 4,589,783 | 5/1986 | Thomas et al. | 374/6 |
| 4,623,561 | 12/1986 | Rosencwaig et al. | 374/5 |
| 4,659,172 | 4/1987 | Cavan | 356/237 |
| 4,681,442 | 7/1987 | Wagner | 356/237 |
| 4,818,118 | 4/1989 | Bantel et al. | 374/7 |

FOREIGN PATENT DOCUMENTS

| | | | |
|---|---|---|---|
| 0157686 | 12/1979 | Japan | 356/237 |
| 0063451 | 4/1985 | Japan | 356/237 |
| 2168494 | 6/1986 | United Kingdom | 374/5 |

OTHER PUBLICATIONS

Kutzscher et al., "Thermal and Infrared Methods for Nondestructive Testing of Adhesive-Bonded Structures," Materials Evaluation, pp. 143-148 (Jul. 1968).

Van der Merve and Jesser, "Descriptions of Low Energy Misfit Dislocation Structures Using the Parabolic Interaction Potential", Material Science and Engineering, A113, 85, 1988.

V. L. Pokrovskii and A. L. Talapov, "Theory of Two-Dimensional Incommensurate Crystals", Soviet Physics-JETP, 51, 134, 1980.

deGennes, "Wetting: Statics and Dynamics" Rev. Mod. Phys. 57, 827, 1985.

Fishman et al., "Surface Selectivity in Four-Wave Mixing", J. Opt. Soc. Am. B, vol. 8, No. 9, Sep. 1991.

Marshall et al., "Thermal Diffusion, Interfacial Thermal Barrier, and Ultrasonic Propagation in $YBa_2Cu_3O_{7-x}$ Thin Films", Submitted Phys. Rev. B, 1991.

Marshall et al., "Ultrasonic Wave Propagation and Barrier-Limited Heat Flow in Thin Films of $YBa_2Cu_3O_{7-x}$", Phys. Rev. B, vol. 43, No. 4, Feb. 1, 1991.

*Primary Examiner*—William A. Cuchlinski, Jr.
*Assistant Examiner*—Diego F. F. Gutierrez

[57] ABSTRACT

A method for the quantitative and qualitative evaluation of a nonuniform interface between a layer and a substrate is disclosed wherein thermal excitation is provided by irradiating the layer and thermal relaxation responsive to this thermal excitation is measured. The measured thermal relaxation is compared to the expected values, obtained from a model derived for the quantitative description of the process of thermal relaxation. The fraction of the deteriorated area of the interface is obtained from the portion of the thermal relaxation which diverges from the expected values.

9 Claims, 4 Drawing Sheets

THE INTERFACE BETWEEN LAYER AND SUBSTRATE

This invention was made with Government support under contract N00014-91-C-0170 awarded by the Office of Naval Research. The Government has certain rights in this invention.

FIELD OF THE INVENTION

The subject invention relates to a new method of evaluation of the quality of adhesion between two contacting materials and more particularly, for testing of thermal conductivity between film and substrate, by defining the fraction of deteriorated thermal contact on the interface area.

BACKGROUND OF THE INVENTION

In semiconductor processing, as in layer growth technology, and in coating of optical substrate processes, it is important to know the quality of intimate contact between film and substrate. Among the well known methods of quality testing of the interface, optical microscopy is often used.

In the method of optical microscopy, a judgement on the adhesion quality is made relying on optical effects on the interface, such as reflection, transmission and scattering of visible light. This method provides evaluation of transparent objects on the scale of several microns. Another method of visual testing is obtained by electron microscopy, which performs similar testing with electrons having wavelengths 3 orders of magnitude less than visible light and thus providing 3 orders of magnitude increased spatial resolution. Since both of the above methods respond primarily to electron susceptibilities of materials, neither allows obtaining direct information on intimate contact of film and substrate lattice structures.

Photothermal excitation and probe techniques became one of the first attempts to get direct information regarding the surface and interface, (U.S. Pat. No. 4,513,384, to Rosencwaig.) Rosencwaig teaches the process of periodic excitation of the sample interface by focused laser beam, generating of a thermal wave inside the sample, probing of the sample by the second focused laser beam, and measuring the reflectivity variation of the probe beam induced by the thermal wave. This method responds directly to the thermal properties of material (thermal conductivity) with spatial resolution limited by the size of the focused laser beam (several microns.) The further development and extensive usage of this method were described in the papers titled "Photoacoustic and Photothermal Phenomena II" Editors: J. C. Murphy et al., Springler Series in Optical Sciences, v.62,1990.

However, low spatial resolution is a principal limitation of the thermal wave method. For detection of amplitude and phase variation of the thermal wave one has to consider both exciting and probe laser beams focused to spots with sizes less than the distance between these spots (ideally, to geometrical point sources). Theoretical limitation for minimal spot size is the laser wavelength—approximately equal to 0.5 micron—which yields several microns as a theoretical spatial resolution limit for thermal wave method.

The aforementioned prior art method does not satisfy the need for much higher resolution for many processes such as coatings or crystal growth. The spatial resolution required for these processes has to be of the order of magnitude of an elementary cell or several elementary cells, which value might be tens or hundreds of Angstroms.

As soon as the variations of intimate contact quality are considered on a scale compared to elementary cell size (or, on the so called mesoscopic scale), the location of perfect or deteriorated areas on the interface is not important. It is crucial for evaluation of the quality of interfaces to measure the fraction of perfect contact, that is the ratio of perfect contact area to the entire area of a contact (interface) and to estimate an average size of mesoscopic contact area.

For example, in the process of crystal growth on a substrate the mismatch between film and substrate lattices which is accumulated along the interface eventually produces dislocations or sublattices (see, for example, Jan H. van der Merve, W. A. Jesser, Material Science and Engineering, A113, 85,1988 and V. L. Pokrovskii and A. L. Talapov, Sov. Phys. JETP,51,134,1980). As a result, the mismatch causes reduction of intimate contact in the range from several to several hundred unit cells, which counts for several hundred Angstroms.

Another possible problem arises with respect to adhesion of a coating to a substrate. Encompassed in this category is a wide variety of processes, such as: sputter deposition, emulsion coating, MOCVD and the like. The macroscopic deteriorations of intimate contact between the deposited coating (that usually strongly absorbs visible light) and the substrate, on the scale of several microns, may be evaluated by the thermal wave method. However the most important question to be solved and which is achieved with the present invention is the determination of the fraction of mesoscopically deteriorated area on the interface.

Analysis of wetting processes, e.g. spreading of a liquid substance over the surface of a solid substrate (P. G. de Gennes, Rev. Mod. Phys. 57,827 (1985)) creates the problem of evaluation of intimate contact between the spreading liquid layer and the substrate. This kind of evaluation is especially important for biophysical and biochemical systems. Intimate contact between a spreading liquid layer and a solid substrate may be adversely effected by impurities, local substrate imperfections etc. Definition of the precise fraction of unwetted substrate is an important characteristics that can not be obtained by the prior art.

Accordingly, it is therefore an object of the subject invention to provide a new method for evaluating quality of intimate contact between film and substrate on the mesoscopic scale. The method of the invention improves spatial resolution by two orders of magnitude compared to the existing methods.

It is another object of the subject invention to provide a new method for evaluating, with spatial resolution on the mesoscopic scale, the quality of a wide variety of coatings deposited on a wide variety of substrates.

It is a further object of the subject invention to provide a new method for evaluating the fraction of unwetted surface of liquid on a substrate with spatial resolution of several hundred Angstroms.

SUMMARY OF THE INVENTION

These and additional objects are accomplished by the subject invention that overcomes the shortcomings of the prior art by providing a new method for evaluation of the quality of the interface between a substrate and a film or layer, based on the detection of relaxation of thermal excitation of the layer. In order to interpret the results of thermal relaxation of the excited layer, a model of thermal relaxation through a nonuniform interface is derived. In this model, the interface is considered as a sequence of mesoscopic adjacent conducting areas and areas with zero thermal conductivity positioned similar to black and white locations of a checker-board. According to this model, thermal parameters of the interface such as thermal conductivity and rate of heat transfer through the interface are described as a function of average size of "black" and "white" areas of such a checker-board. Heat transfer inside the film and through the interface causes thermal relaxation which is measured.

The proposed model describes the expected values of thermal relaxation signals as a function of thermal properties of the interface, as average sizes of "black" and "white" thermal contact areas on the interface.

In accordance with the subject invention, measured kinetics of thermal relaxation are compared with respect to data obtained from a model, particularly for a later stage of thermal relaxation. The later stage of thermal relaxation is characterized by a relatively invariable temperature profile on the interface, and corresponds to several half widths of a fast thermal relaxation on the surface. The amplitude and temporal kinetics of the detected signal, being a function of geometry of the mesoscopic structure of the interface, provide information on the interface thermal conditions, as a ratio of "black" and "white" areas and average size of mesoscopic spots on the interface.

In the preferred embodiment, thermal excitation along the interface is provided by producing a transient grating on the surface or interface. To produce the transient grating, two interfering coherent light beams intersect on the surface (or interface), which results in a sinusoidal profile of heated and non-heated stripes on the surface (or interface). To detect thermal relaxation of the transient grating the sample is irradiated by the third (so called probe) laser beam, temporally delayed relative to the exciting beams. This probe delay time is an important independent variable of the measured thermal relaxation. In the preferred embodiment, both exciting and probe beams originate from the same laser, and the distance between stripes (the fringe spacing) is fixed. If the thermal diffusivity of the tested sample needs to be measured the variation of fringe spacing is used. Further objects and advantages of the subject invention will become apparent from the following detailed description taken in conjunction with the drawings in which:

DETAILED DESCRIPTION OF THE PREFERRED EMBODIMENT

As discussed above the evaluation of the interface between the thin film and the sample is provided by measurement of kinetics of thermal relaxation of the nonuniformly heated sample. To describe the kinetics a mathematical model was developed by the author of the present invention for heat transfer through the mesoscopically nonuniform interface.

Figure 1:
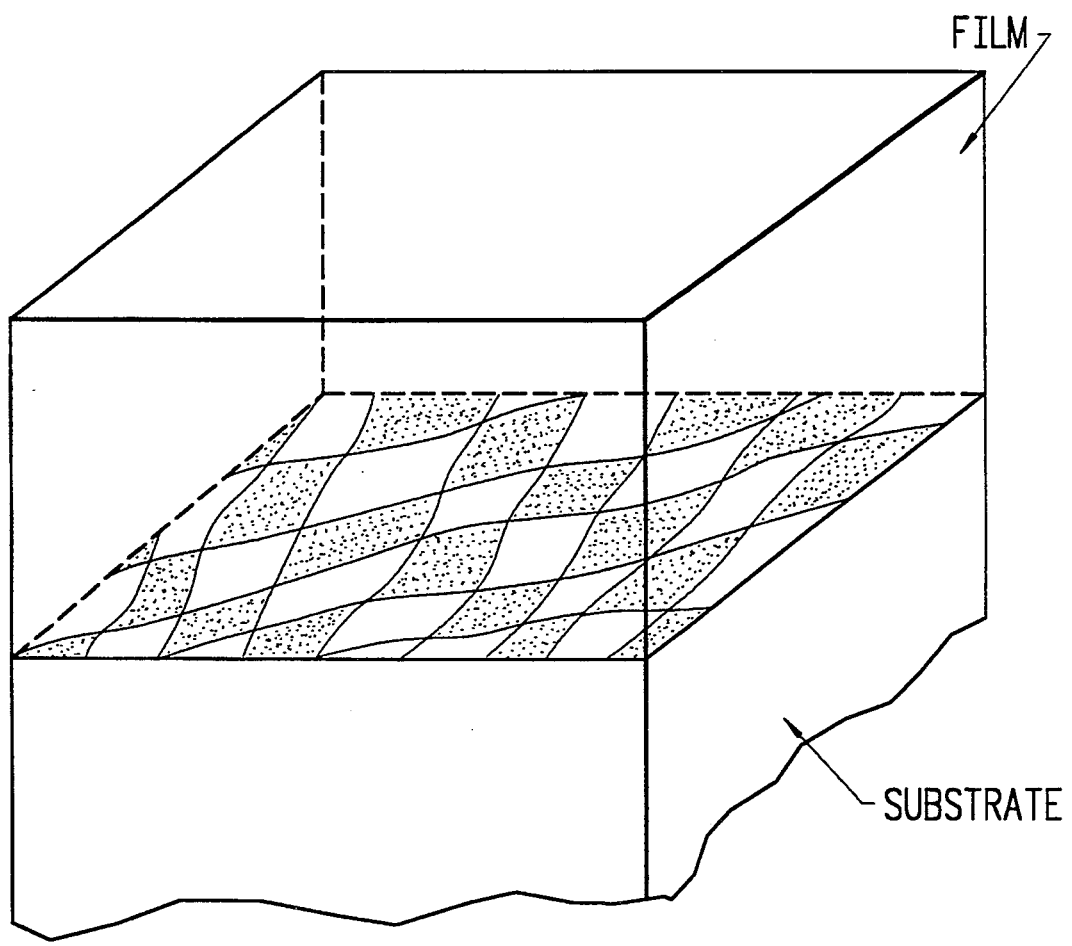
FIG. 1 is a graphic view of the mesoscopically nonuniform interface.

According to the model, the interface is considered similar to a checker-board, with "black" areas that have reduced thermal contact and "white" ones that have no thermal contact with the substrate. If a film of thickness L is grown on the substrate with infinite thermal conductivity, the substrate temperature Ts will be zero (see FIG. 1). The interface plane (Z=0) is characterized by variation of thermal conductivity both in X- and Y-directions with average size d for "white" areas. Boundary conditions for heat transfer are dT/dZ=0 at "white" areas (which implies that heat does not go through "white" areas), and T=0 at "black" areas, which means that "black" areas provide ideal heat transfer, limited only by the acoustic properties of conducting materials in thermal contact with the infinitely thermally conducting substrate. It is always suggested that d<<L. With the initial condition T=To throughout the sample, one is interested in the temperature kinetics both in the volume and on the surface.

In the steady-state, the diffusion equation is converted to the Laplace equation:

$$\frac{\partial^2 T}{\partial X^2} + \frac{\partial^2 T}{\partial Y^2} + \frac{\partial^2 T}{\partial Z^2} = 0 \qquad (1)$$

The solution of (1) far from the interface (Z>>d) is a linear function of Z:

$$T = T_{eff} + T_o \frac{Z}{L}, \qquad (2)$$

$T_{eff}$ is the average temperature at the interface given by $$T_{eff} = \nu T_w \qquad (3)$$

where $T_w$ is the average temperature of a "white" area on the interface and $\nu$ is the ratio of "white" area to the entire area of the interface, $T_w \approx T_o d/L$. The effective boundary condition at the interface is defined by $T_{eff}$. Another form of the boundary condition at the interface is:

$$\kappa \frac{dT}{dZ} = A T_{eff} \qquad (4)$$

Combining (2), (3) and (4) yields ($\kappa$- thermal diffusivity of the film):

$$A = \kappa/\nu d \qquad (5)$$

Equation (5) provides an expression for A, the rate of heat transfer through the interface. This value can be measured experimentally, producing a method for determining $\nu d$ (if the thermal diffusivity is measured independently). To measure thermal diffusivity, the prior art thermal wave method or the transient grating method with the variable fringe spacing may be used. Measurement of A provides a value for $\nu d$, e.g. product of average size and fraction of reduced thermal contact. To obtain values of both $\nu$ (the fraction of reduced contact) and d (the average size of area with reduced conductivity) separately, the second independent measurement is required. This is a measurement of temperature kinetics on the sample surface. The technique of this measurement, as well as technique for measurement of the value of A, will be described in the next section.

On the surface, the temperature of "black" areas is given by $T_b=0$, and on the "white" areas heat is propagating primarily in X and Y directions (FIG. 1):

$$T(X,Y) = \exp\left[-kt\left(\frac{m^2\pi^2}{d_i^2} + \frac{n^2\pi^2}{d_j^2}\right)\right]\sin\frac{m\pi}{d_i}(X - X_i)\sin\frac{n\pi}{d_j}(Y - Y_j) \quad (6)$$

The longest of relaxation terms (6) $\tau_i = d_i^2/\pi^2 K$ is responsible for the heat transfer along the surface area over distance d. Measuring this time constant experimentally one obtains a value for d. Combination of equations (5) and (7) provides separate measurements of both average size and fraction of non-conduction areas on the interface. The described measurement is effective if "black" and "white" areas of the interface differ by not more than an order of magnitude ($0.1 < \gamma < 1.0$) which is limited by the accuracy of fitting of experimental data by computer calculations (see C. D. Marchall et al. Phys Rev B submitted, 1991).

In the model developed here, the presence of non-conducting areas results in a decrease, compared to the theoretical value, of the rate of heat flow though the interface, and the presence of conducting areas provides a rapid temperature drop at the surface, following the instant of sample heating.

Figure 2:
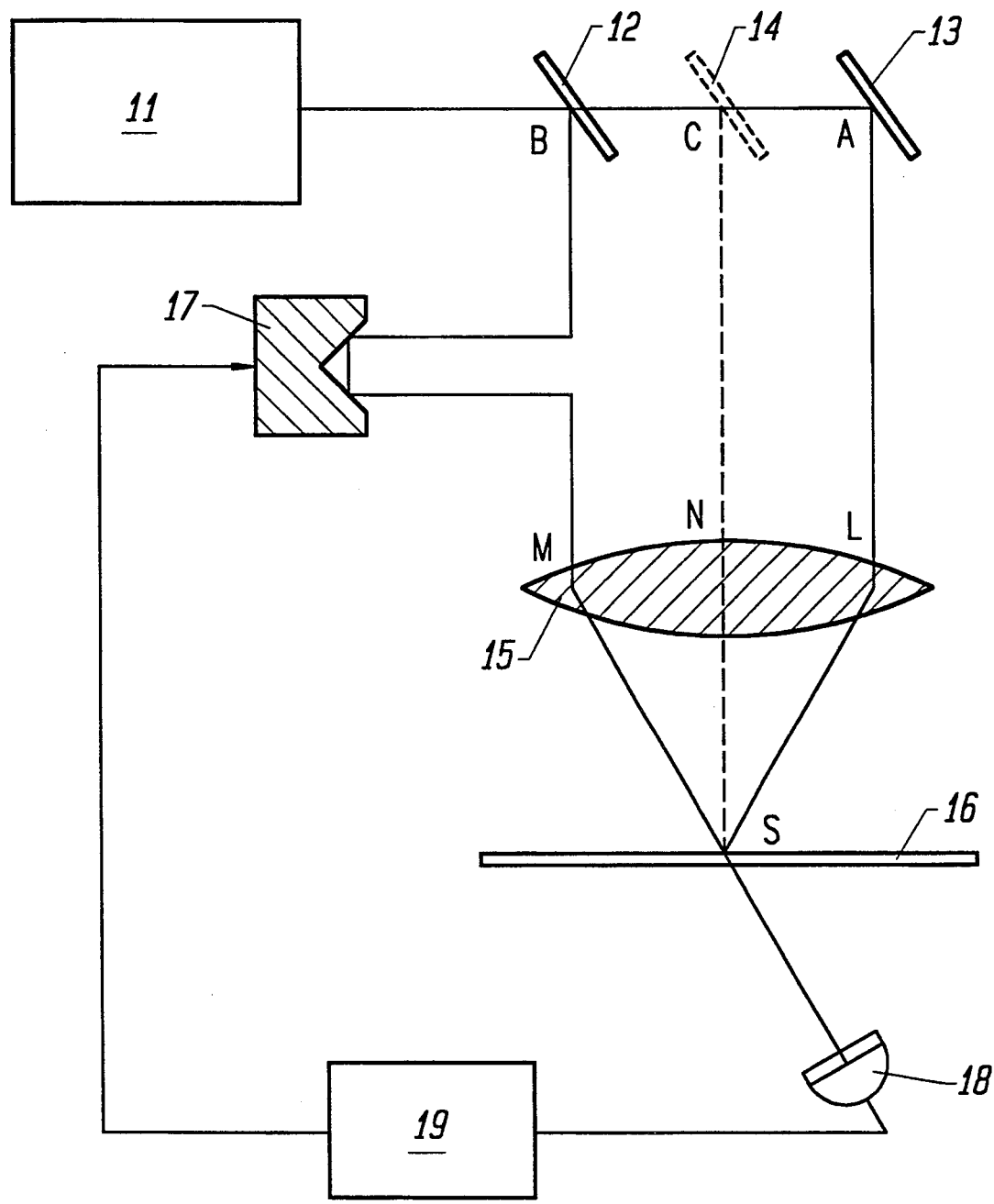
FIG. 2 is a basic scheme of sample testing using laser excitation and probe beam.

As described above, to evaluate the quality of interface, one has to initiate thermal excitation of a sample and observe the thermal relaxation. For this purpose, in the present invention the technique of the sample thermal excitation and probe by short laser pulses is employed. FIG. 2 shows the basic scheme of the sample test using a short pulse laser (for example, picosecond Nd-YAG laser). The laser beam generated by laser 11, is split by the beam splitters 12 and 13 into two beams: pump beam ALS and probe beam BMS respectively. Both pump and probe beams are focused by the lense 15 onto the sample 16. The probe pulse is delayed, before hitting the lense 15, by the optical delay line 17. Probe beam BMS is detected after passing across the sample 16 by the optical detector 18 and the signal is analyzed as a function of delay line position, by the computer 19. The excitation induced by the pump beam ALS causes change of the optical density of the sample 16 which is probed by the probe beam BMS.

Since change of the optical density is usually small and, in respect to that, variation of the detected signal as a function of delay line position is difficult to recover, to improve the detection sensitivity in a preferred embodiment a transient grating technique is used. To produce the transient grating one has to use the additional beam splitter 14 to split off additional beam CNS of the pump beam ALS and to focus it on the sample 16 in temporal coincidence with the pump beam ALS.

Figure 3:
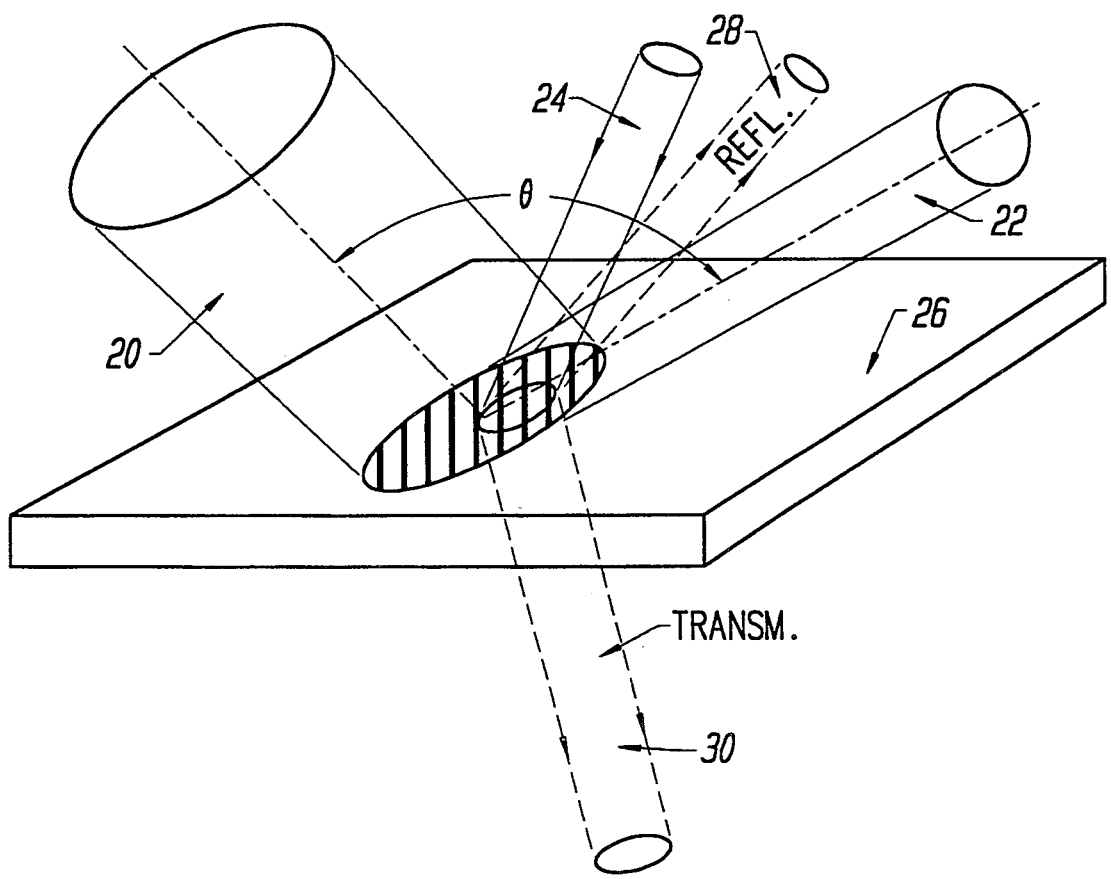
FIG. 3 is a graphic representation of excitation and detection of the signal in transient grating geometry.

At FIG. 3, one example of a geometry for excitation and probe beams in the transient grating technique is schematically described.

The transient grating is produced using the interference of two exciting (or pumping) beams 20 and 22 interfering at the sample 26. The third beam 24, diffracted by the transient grating is delayed relative to the exciting beams to obtain kinetics of thermal relaxation as above described.

In a preferred embodiment the laser beam is split in two beams 20 and 22, and these two exciting beams intersect at the sample 26 with the angle $\theta$ between them. Since these two beams originate from the same laser they are coherent and can interfere. The interference produces spatially periodic modulation of optical intensity, which in turn produces periodic the thermal excitation of the sample 26 placed in front of beams 20 and 22. Along the sample surface, periodic excitation produces periodic fringes of heat absorption with the fringe spacing depicted by the thick lines in FIG. 3:

$$F.S. = \frac{\lambda}{2\sin\theta/2}$$

where $\lambda$ is the wavelength of light. The third beam 24, which is the probe, is directed to the sample 26 with a variable time delay. This third beam is usually derived from the same laser, but it may be obtained from another laser, for example, a dye-laser. The third beam 24 is diffracted by the transient grating producing the diffracted beams 28 and 30, which provide the optical signals detected by light detectors (phototubes or photodiodes). Diffraction causes angular separation of these signal beams 28 and/or 30 from both exciting beams 20 and 22, and probe beam 24. The transient grating technique furnishes the signal measurement with zero offset, strongly diminishing linear noise because neither probe nor pump beams enter the detecting system. Though the diffraction efficiency of the transient grating for thin films is not very high ($<10^{-4}$), the absolute number of photons is usually enough for reliable registration of the diffracted signal over several orders of magnitude.

An alternative choice of geometry places the probe and excitation beams in an apposite sense of incidence with respect to the interface. This is an appropriate but not essential, geometry where both substrate and layer are substantially transparent to probe and excitation radiation. In either geometry the use of either a reflected or transmitted signal beams 28 or 30 for measurement purposes consistent with details of the specific sample.

The important development of the transient grating technique was disclosed by Fishman et al. in paper titled "Surface selectivity in four wave mixing:transient gratings as a theoretical and experimental example", Journal of the Optical Society of America, v8, No 9 (1991). Transient grating measurements are available for both transmission and reflection geometries (FIG. 3). In the transmission geometry, all sections of the sample 26 parallel to the interface equally contribute to the diffracted signal. In the reflected signal only the contribution from a thin layer close to the interface is substantial. This allows separation of different components of the thermal relaxation process.

Figure 4:
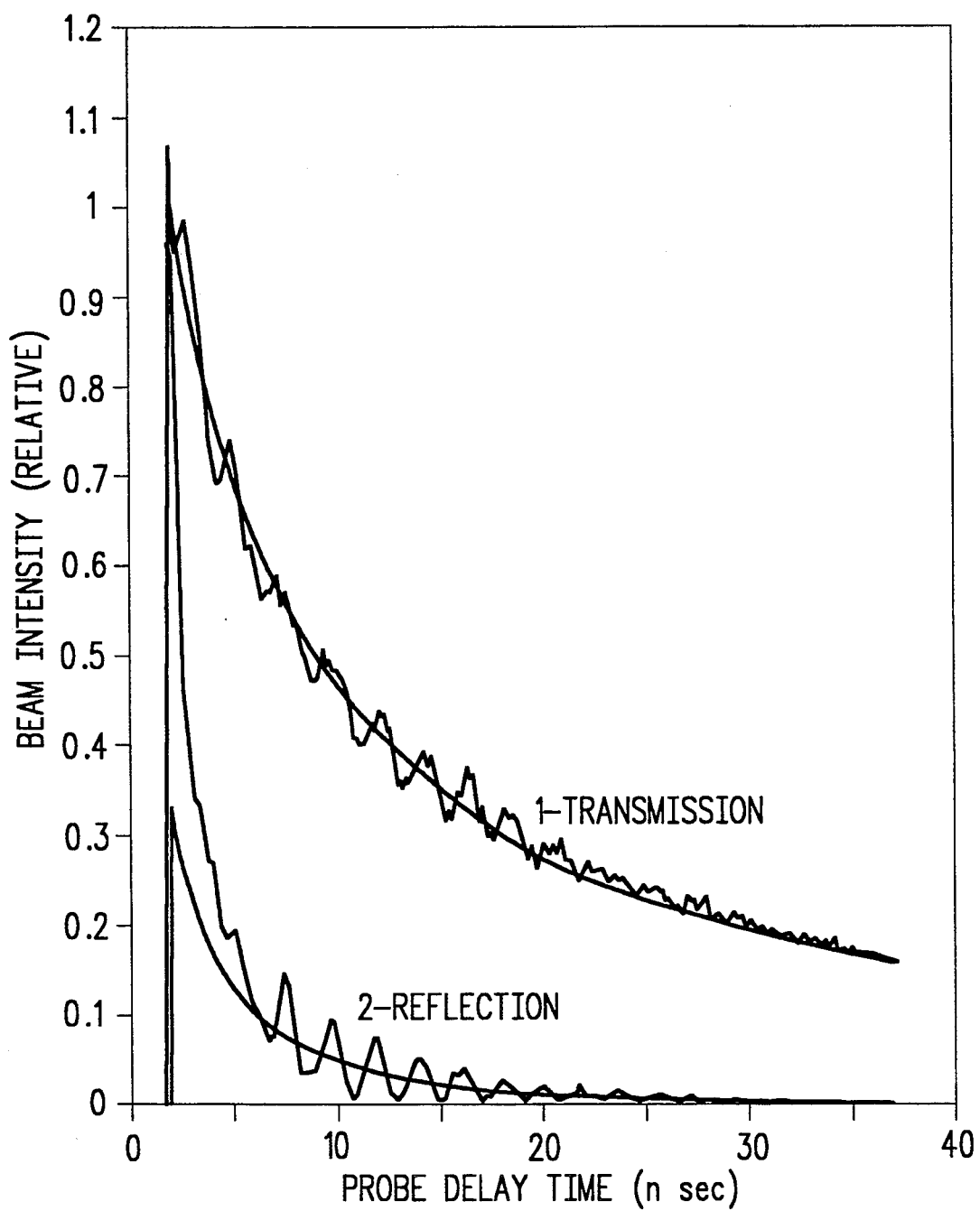
FIG. 4 is a graph showing the relationship between experimental measurement and expected values obtained from the model.

The results of observation of thermal relaxation of a transient grating induced in 220 nm YBCO film on MgO substrate are depicted in FIG. 4. To obtain this result the transient grating with fringe spacing F.S.=10 microns was excited using two beams derived from a dye laser that was pumped by a picosecond Nd-YAG laser. The transient grating relaxation was probed by the third dye laser pulse delayed relative to the exciting pulse for (0–50)nsec. The fitting procedure was conducted for the experimental results given in FIG. 4, curve 1, for transmission geometry, using a mathematical expression for one-dimensional heat transfer to obtain the average rate of heat transfer A. The mathematical equation for one-dimensional heat transfer are known from a previous publication (see C. D. Marshall et al).

In FIG. 4, curve 1 shows the degree of coincidence of the experimental data (wavy curve) and expected data (smooth curve) being superimposed over each other. Using the obtained value of A, the average size of nonconducting areas on the interface d was calculated with the coefficient equal to the ratio of nonconducting area to the entire area of the interface.

In FIG. 4, curve 2 shows intensity of the reflected diffracted beam as a function of delay time (reflection geometry). The fitting procedure, similar to the transmission geometry is used for the reflection geometry to obtain the comparison of experimental and theoretical data. The initial part of the curve 2 shows the fast temperature drop on the time scale of 600 psec, followed by much slower decay. This initial drop corresponds to thermal relaxation of the conducting area on the interface. The fast process of temperature drop involves only a narrow layer close to the interface (10% of the sample thickness), and practically does not manifest itself in the transmission experiment. The ratio of the fast and the slow reflection components provided an estimate of the fraction of deteriorated contact area ($v=0.35$). The ratio of amplitudes of calculated and experimentally obtained signals agree as shown above with the ratio of the nonconducting area to the entire interface area. Therefore both average sizes of conducting and nonconducting areas on the interface are obtained.

I claim:

1. A method for evaluation of the quality of the interface between a layer disposed on a substrate, said interface being nonuniform in adhesion of said layer and said substrate, comprising the steps of:
   providing a model of expected values for quantitative description of the process of thermal relaxation in the nonuniform interface between layer and substrate;
   irradiating said layer with a plurality of laser beams to provide a non-uniform thermal excitation across said layer;
   measuring thermal relaxation of said thermal excitation;
   comparing said thermal relaxation of said thermal excitation with said expected values for the later stage of the thermal process in said interface obtained from said model;
   evaluating mismatch of said layer with said substrate by selecting the portion of said thermal relaxation that diverges from the expected values.

2. The method of claim 1 wherein said nonuniform thermal excitation is periodic.

3. The method of claim 1 where said step of irradiating to provide thermal excitation is a transient grating.

4. The method of claim 3 wherein said transient grating results from concurrent irradiation of said layer by said laser beams including two coherent exciting beams of radiation derived from a first radiation source.

5. The method of claim 4 wherein said thermal relaxation is measured by irradiating said layer by a third beam of probe radiation and detecting of a diffracted component of said third beam, said third beam being temporally delayed relative to said two coherent exciting beams.

6. The method of claim 5 wherein said third beam of probe radiation is derived from said first radiation source.

7. The method of claim 5 wherein said third beam is obtained from another radiation source, said another radiation source non coherent with said first radiation source.

8. The method of claim 5 wherein said step of irradiating said layer by a third beam is accomplished with said third beam of probe radiation incident on said layer, said layer being substantially transparent to said probe radiation.

9. The method of claim 5 wherein said step of irradiating said layer by a third beam is accomplished with said third beam of probe radiation incident on said substrate, said substrate being substantially transparent to said probe radiation.

* * * * *